United States Patent
Collins et al.

(10) Patent No.: US 8,337,557 B2
(45) Date of Patent: Dec. 25, 2012

(54) APPARATUS AND KIT FOR INJECTING A CURABLE BIOMATERIAL INTO AN INTERVERTEBRAL SPACE

(75) Inventors: Keith Collins, Milford, CT (US); Thomas G. Wilson, Guilford, CT (US); Andrew Carter, Trumbull, CT (US)

(73) Assignee: Spine Wave, Inc., Shelton, CT (US)

( * ) Notice: Subject to any disclaimer, the term of this patent is extended or adjusted under 35 U.S.C. 154(b) by 1862 days.

(21) Appl. No.: 11/170,657

(22) Filed: Jun. 29, 2005

(65) Prior Publication Data

US 2006/0004326 A1    Jan. 5, 2006

Related U.S. Application Data

(60) Provisional application No. 60/583,665, filed on Jun. 29, 2004.

(51) Int. Cl.
*A61F 2/44* (2006.01)
(52) U.S. Cl. .................................................. 623/17.12
(58) Field of Classification Search .................... 606/53, 606/92–94, 192; 623/17.11, 17.12, 17.16; 604/60, 164.11
See application file for complete search history.

(56) References Cited

U.S. PATENT DOCUMENTS

| | | |
|---|---|---|
| 3,893,445 A | 7/1975 | Hofsess |
| 4,142,517 A | 3/1979 | Stavropoulos et al. |
| 4,313,434 A | 2/1982 | Segal |
| 4,492,576 A | 1/1985 | Dragan |
| 4,684,363 A | 8/1987 | Ari et al. |
| 4,772,287 A | 9/1988 | Ray et al. |
| 4,793,351 A | 12/1988 | Landman et al. |
| 4,969,888 A | 11/1990 | Scholten et al. |
| 5,108,404 A | 4/1992 | Scholten et al. |
| 5,300,035 A | 4/1994 | Clement |
| 5,331,975 A | 7/1994 | Bonutti |
| 5,344,439 A | 9/1994 | Otten |
| 5,380,334 A | 1/1995 | Torrie et al. |
| 5,431,676 A | 7/1995 | Dubrul et al. |
| 5,454,365 A | 10/1995 | Bonutti |

(Continued)

FOREIGN PATENT DOCUMENTS

EP    0 277 282    8/1991

(Continued)

OTHER PUBLICATIONS

Premarket Notification [510(k)] Summary, "Kyphx Directional Inflatable Bone Tamps", Kyphx Directional Inflatable Bone Tamp-Traditional 510(k), Kyphon Inc., Sep. 15, 2003, 5 pages).

(Continued)

*Primary Examiner* — Kevin T Truong
*Assistant Examiner* — Michael Araj
(74) *Attorney, Agent, or Firm* — Hoffmann & Baron, LLP

(57) ABSTRACT

A kit of parts is provided that comprises: a cannula, the distal end of the cannula adapted to be inserted through the disc annulus; an injection needle, the distal end adapted to be inserted into the proximal end of the cannula and configured for relatively close sliding fit therewithin; and a syringe for containing a quantity of curable biomaterial, the syringe adapted to be coupled to the proximal end of the needle and to inject the biomaterial into the needle under pressure. The kit may further comprise a quantity of curable biomaterial that is selected to have upon curing strong adhesive properties such as a protein polymer.

17 Claims, 12 Drawing Sheets

U.S. PATENT DOCUMENTS

| | | |
|---|---|---|
| 5,514,153 A | 5/1996 | Bonutti |
| 5,549,565 A | 8/1996 | Ryan et al. |
| 5,562,736 A | 10/1996 | Ray et al. |
| 5,667,520 A | 9/1997 | Bonutti |
| 5,685,826 A | 11/1997 | Bonutti |
| 5,720,726 A | 2/1998 | Marcadis et al. |
| 5,752,969 A | 5/1998 | Cunci et al. |
| 5,762,629 A | 6/1998 | Kambin |
| 5,810,769 A * | 9/1998 | Schlegel et al. ............... 604/59 |
| 5,817,303 A | 10/1998 | Stedronsky et al. |
| 5,827,318 A | 10/1998 | Bonutti |
| 5,860,997 A | 1/1999 | Bonutti |
| 5,888,220 A | 3/1999 | Felt et al. |
| 5,954,739 A | 9/1999 | Bonutti |
| 5,968,062 A | 10/1999 | Thomas et al. |
| 6,017,305 A | 1/2000 | Bonutti |
| 6,033,654 A | 3/2000 | Stedronsky et al. |
| 6,039,761 A | 3/2000 | Li et al. |
| 6,042,596 A | 3/2000 | Bonutti |
| 6,083,202 A * | 7/2000 | Smith ..................... 604/164.01 |
| 6,135,999 A | 10/2000 | Fanton et al. |
| 6,174,311 B1 | 1/2001 | Branch et al. |
| 6,187,023 B1 | 2/2001 | Bonutti |
| 6,187,048 B1 | 2/2001 | Milner |
| 6,210,397 B1 | 4/2001 | Aboul-Hosn et al. |
| 6,224,630 B1 | 5/2001 | Bao et al. |
| 6,245,107 B1 | 6/2001 | Ferree |
| 6,248,131 B1 | 6/2001 | Felt et al. |
| 6,264,659 B1 | 7/2001 | Ross et al. |
| 6,306,177 B1 | 10/2001 | Felt et al. |
| 6,370,420 B1 | 4/2002 | Kraft |
| 6,371,990 B1 | 4/2002 | Ferree |
| 6,402,784 B1 | 6/2002 | Wardlaw |
| 6,423,333 B1 | 7/2002 | Stedronsky et al. |
| 6,436,143 B1 | 8/2002 | Ross et al. |
| 6,443,988 B2 | 9/2002 | Felt et al. |
| 6,558,390 B2 | 5/2003 | Cragg |
| 6,579,291 B1 | 6/2003 | Keith et al. |
| 6,620,162 B2 * | 9/2003 | Kuslich et al. .................. 606/53 |
| 6,805,695 B2 | 10/2004 | Keith et al. |
| 6,981,981 B2 | 1/2006 | Reiley et al. |
| 2002/0045942 A1 | 4/2002 | Ham |
| 2002/0147497 A1 * | 10/2002 | Belef et al. .................. 623/17.12 |
| 2003/0009227 A1 | 1/2003 | Lambrecht et al. |
| 2003/0033017 A1 | 2/2003 | Lotz et al. |
| 2003/0082169 A1 | 5/2003 | Boyd |
| 2003/0083641 A1 | 5/2003 | Angel et al. |
| 2003/0083642 A1 * | 5/2003 | Boyd et al. .................... 604/506 |
| 2003/0209455 A1 * | 11/2003 | Pynson et al. ................. 206/264 |
| 2004/0059339 A1 | 3/2004 | Roehm, III et al. |
| 2004/0073213 A1 | 4/2004 | Serhan et al. |
| 2004/0098017 A1 | 5/2004 | Sabb et al. |
| 2004/0122367 A1 * | 6/2004 | Sculati ......................... 604/140 |
| 2004/0186471 A1 | 9/2004 | Trieu |
| 2004/0229878 A1 | 11/2004 | DiMauro et al. |
| 2005/0070913 A1 | 3/2005 | Milbocker et al. |
| 2005/0102030 A1 | 5/2005 | Yuksel et al. |
| 2005/0209555 A1 | 9/2005 | Middleton et al. |
| 2005/0209601 A1 | 9/2005 | Bowman et al. |
| 2005/0209602 A1 | 9/2005 | Bowman et al. |
| 2005/0234425 A1 | 10/2005 | Miller et al. |

FOREIGN PATENT DOCUMENTS

| | | |
|---|---|---|
| FR | 2 639 823 | 12/1988 |

OTHER PUBLICATIONS

510(k) Summary of Safety and Effectiveness, "KyphX™ Inflatable Bone Tamp", Feb. 14, 2001, 5 pages.

Boyd, Lawrence M., Mahar, Andrew and Cappello, Joseph, "Injectable Biomaterials for Augmentation of the Nucleus Pulposus", International Symposium-Non-Fusion Techniques in Spinal Surgery, Feb. 14, 2003, 12pages.

Mahar et al., "Biomechanical Efficacy of a Protein Polymer Hydrogel for Inter-Vertebral Nucleus Augmentation and Replacement", World Congress of Biomechanics, Calgay, Canada, Aug. 5, 2002, 4 pages.

Kitchel, Scott and Cappello, Joseph, "Injectable Biomaterials for Augmentation of the Nucleus Pulposus", http://127.0.0.1:8080/SAS3C1/presentation_list8.php, Apr. 25, 2005, 6 pages.

Garfin, Steven R. Yuan, Hansen A., and Reiley, Mark A., "Kyphoplasty and Vertebroplasty for the Treatment of Painful Osteoporatic Compression Fractures", Spine, vol. 2, No. 14, pp. 1511-1515, 2001© Lippincott Williams & Wilkins, Inc.5 pages.

Lieberman et al., "Initial Outcome and Efficacy of "Kyphoplasty" in the Treatment of Painful Osteoporatic Vertebral Compression Fractures", Spine, vol. 26, No. 14, pp. 1631-1638, 8 pages.

* cited by examiner

APPARATUS AND KIT FOR INJECTING A CURABLE BIOMATERIAL INTO AN INTERVERTEBRAL SPACE

REFERENCE TO RELATED APPLICATION

The present application claims priority to provisional application No. 60/583,665, entitled "SYSTEMS AND METHODS FOR INJECTING A CURABLE BIOMATERIAL INTO AN INTERVERTEBRAL SPACE", filed on Jun. 29, 2004, the entire disclosure of which is incorporated herein by reference.

BACKGROUND OF THE INVENTION

The present invention relates to systems and methods for the treatment of the spine, and especially the interbody disc space. More specifically, the invention concerns the injection of a biomaterial into a spinal space, such as the intradiscal space.

Spine fusion procedures represent the state of the art treatment for intervertebral disc problems, which generally involve open surgery and the use of interbody fusion cages and spinal fixation systems to stabilize the fusion site. An alternative treatment under evaluation is to replace or augment the disc or nucleus pulposus with a prosthetic device. Examples of some devices currently under investigation include in-situ cured polymers such as polyurethanes and protein polymers, which may have properties varying from a rubbery hydrogel to a rigid plastic. Problems associated with these devices occur during insertion, whereby the pressure required to fill the disc space can cause leakage of the material into sensitive adjacent areas.

A number of devices are available for distracting vertebral bodies or for injecting material into the disc. Some devices are capable of both distraction and injection using the same instrument. These types of devices use a deflated balloon attached to a cannula and inserted between the vertebral bodies. The balloon is inflated with a prosthetic fluid through the cannula to distract the vertebral bodies. This requires high-pressure delivery of the fluid to achieve the pressure needed to distract the vertebral bodies and the balloon and fluid permanently remain in the disc space. Alternatively, a separate device is used to inject the prosthetic fluid around the balloon and the balloon is used strictly for distraction after which it is deflated and removed.

U.S. Pat. No. 4,772,287 ("Ray I") discloses a bladder injected with thixotropic gel implanted between two vertebral bodies to restore the disc height. The technique described requires that the vertebral bodies are first distracted and a bore drilled to allow for insertion of the bladder.

U.S. Pat. No. 5,562,736 ("Ray II") discloses a method for implanting a prosthetic disc nucleus. Ray II discloses cutting a first and second flap in the annulus. The flaps provide access to the nucleus. Ray II then discloses using an inflatable jack to distract the disc space prior to insertion of the prosthetic spinal disc nucleus. The jack has a deflated balloon on its end that is inserted into the nucleus through one of the flaps. The balloon is inflated with fluid causing the vertebral bodies to distract. Once the vertebral bodies are sufficiently distracted the fluid flow is stopped and the prosthetic spinal disc nucleus is inserted through the other flap. The balloon is then deflated and the second prosthetic spinal disc nucleus is inserted. The flaps are closed and placed in contact with the annulus by a suture, staple or glue.

U.S. Pat. No. 6,187,048 ("Milner") discloses an implant for an intervertebral disc nucleus pulposus prosthesis made from a conformable, in-situ curable, material which is resiliently deformable. Milner discloses removing the nucleus material, then either injecting through the annulus or creating an opening in the annulus to deliver a curable material under pressure into the nucleus space. The pressure is necessary to ensure conformation to the nucleus space and/or to increase the internal pressure of the disc space to distract the vertebral bodies. The amount of pressure needed to distract the disc space is high and may allow the material to flow through cracks or voids in the annulus into the disc space. Milner also describes an embodiment where the curable material is injected into a flexible container that is inserted first into the nucleus space in a deflated state and inflated by the material as the material is injected. This method relies on the pressure of the fluid as it is injected to distract the vertebral bodies. Although this avoids the problem of the material leaking through the annulus, it imposes certain constraints such as designing a cover of the correct shape and size suitable for safe injection of the curable material and prevention of leakage of the material from the cover once filled.

U.S. Pat. No. 6,248,131 ("Felt") describes distracting and injecting at the same time using a balloon device. The balloon can be used as a shell for containing the injected curable biomaterial and also used as a distraction means as the material is injected. Another embodiment describes the balloon as a cylinder shape which when inflated inside the disc space bears against the endplates for the vertebral bodies and distracts them. Then a second device is used to inject the curable biomaterial around the balloon cylinder. The material is allowed to cure and then the balloon is removed and a second curable biomaterial can be injected into the space left where the balloon was. In sum, when Felt discloses injecting material outside of the balloon, Felt discloses using a second device to carry out the injection. Insertion of this second device into the disc should typically require a second breach of the annulus fibrosus.

Much of the prior art contemplates free injection of biomaterial into a spinal space which may lead to uncontrolled leakage. The art also describes injection of the material into a deflated balloon, which requires leaving the balloon inside the disc space. Lastly, some methods require insertion under high pressure, thereby creating a potential for the prosthetic fluid to ooze or seep out of the disc space intra-operatively.

There is therefore a need for a system and method for introducing a biomaterial into a spinal space that is not prone to the problems of the prior art, especially the leakage problem experienced by the high pressure injection systems. This need extends to systems that can be easily utilized in a minimally invasive procedure.

SUMMARY OF THE INVENTION

To address these needs, an apparatus for introducing a curable biomaterial into a spinal disc nucleus pulposus, comprises: an injection needle sized for introduction into the nucleus pulposus; a syringe operable to inject a curable biomaterial contained in the syringe under fluid pressure through the injection needle; and a valve coupled between the injection needle and the syringe. The valve is operable in an open position to permit passage of the biomaterial from the syringe into the needle under fluid pressure, and in a closed position to maintain the fluid pressure of the injected biomaterial within the nucleus. In certain embodiments, the needle has a relatively smooth outer surface and a substantially constant outer diameter over its length.

The apparatus may further comprise an outer docking cannula that is sized and configured for piercing through the disc annulus and for docking thereto. The docking cannula may be relatively thin-walled, having a substantially constant outer diameter and an inner opening extending therethrough of substantially constant inner diameter. The cannula inner diameter may be sized for relatively close sliding fit with the outer diameter of the needle. In certain embodiments, the cannula is in the range of 16-20 gage, while the needle may be in the range of 18-22 gage.

In certain aspects of the invention, the cannula has a predetermined length from its distal end which is adapted to pierce through the annulus and its proximal end which is adapted to receive the needle. The predetermined length may be selected to allow the proximal end of the cannula to reside outside the body of a patient when the distal end extends through the annulus.

In further aspects, the cannula has an anchor portion for docking the cannula to the annulus. The anchor portion may comprises threads on the outer surface of the cannula along an extent of the cannula at its distal end for threadably engaging the disc annulus. A flange may be disposed on the cannula adjacent the threads, with the flange sized and configured to contact the outer surface of the annulus when the cannula is docked thereto for providing and maintaining a seal between the annulus and the flange.

In another embodiment of the invention, a kit of parts is provided for use in treating a damaged or diseased spinal disc having an outer annulus and an inner nucleus pulposus. The kit comprises: a cannula having a distal end and a proximal end, the distal end of the cannula adapted to be inserted through the disc annulus; an injection needle having a distal end and a proximal end, the distal end adapted to be inserted into the proximal end of the cannula and configured for relatively close sliding fit therewithin; and a syringe for containing a quantity of curable biomaterial, the syringe adapted to be coupled to the proximal end of the needle and to inject the biomaterial into the needle under pressure. The syringe of the kit may include a valve coupled thereto, the valve being operable in an open position to permit passage of the biomaterial from the syringe under pressure, and in a closed position to maintain the pressure of the injected material into the needle.

In certain embodiments, the kit further comprises a quantity of curable biomaterial. The biomaterial may be selected to have upon curing strong adhesive properties and may contain a protein polymer.

It is one object of the present invention to provide devices and systems for introducing a biomaterial into an intradiscal space for the treatment of various spinal disorders. Further objects are achieved by aspects of the invention that allow for maintaining fluid pressure within the intradiscal space as it is filled with the biomaterial. Other objects and certain benefits of the invention will become apparent upon consideration of the following written description taken together with the accompanying figures.

DESCRIPTION OF THE PREFERRED EMBODIMENTS

Figure 1:
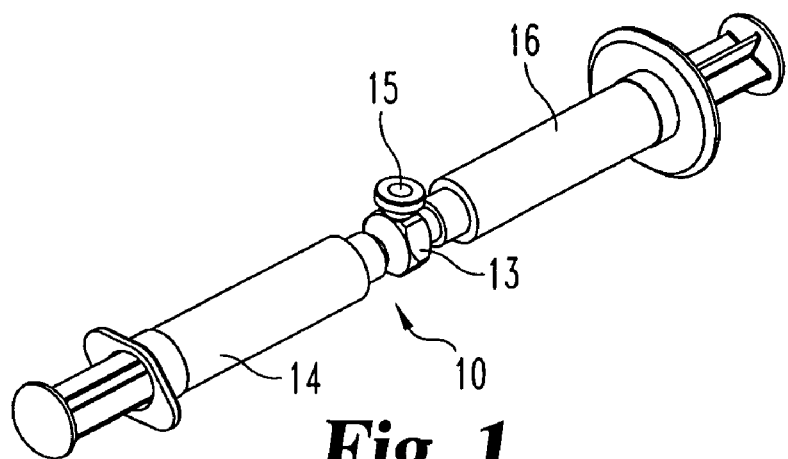
FIG. 1 is a perspective view of a mixing system for mixing an injectable biomaterial.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In one embodiment of the invention, adjacent vertebral bodies are distracted (by a non compliant balloon) at a predetermined pressure, such as at 200 psi (13 atmospheres). Using a non-compliant balloon restricts the lateral dimension of the balloon and ensures that there is no lateral loading, or pressurization of the annulus, thereby avoiding the risk of damaging the annulus. The balloon (and thereby the distraction device) is then removed allowing the distracted vertebral bodies to remain distracted due to the natural stretching of the surrounding ligaments. The distraction with the balloon under pressure is held for a period of time sufficient to stretch the ligaments and to cause the distraction to be maintained even after the balloon is removed. This period of time will vary between patients; however, in certain procedures a period of about 20-30 seconds has been sufficient, while in other cases the period may be several minutes. While there may be some slight contraction of the ligaments initially, the vertebral bodies will remain spaced apart at a substantially desired spacing for some time to then enable introduction of biomaterial into the distracted disc space.

The biomaterial is sealably introduced under pressure that is not as high as used for the distraction step but that is sufficient so that the biomaterial will completely fill the space (or the partial space in a partial discectomy). Moreover, the injection pressure for the biomaterial is sufficient to recover any small amount of contraction that may occur when the balloon is removed. In accordance with one feature of the invention, the injection of the biomaterial occurs under low pressure. This pressure is nominally less than 100 psi, and in specific embodiments is in the range of 25-40 psi. A vent is used to exhaust the disc space and allow body fluid and/or air as well as biomaterial to seep out when the space is filled. Seepage of biomaterial indicates a complete fill of the disc space.

The low pressure on the biomaterial is held until the biomaterial is cured. This cure time is material dependent, but often falls in the range of about five minutes. Maintaining the pressure until curing also maintains the distracted disc space under hydrostatic pressure. Even under the low pressure, a seal must be provided around the opening in the annulus through which biomaterial is introduced. The seal in one arrangement is disposed on the material injection tube and is applied against the exterior surface of the annulus adjacent the opening.

In a particular procedure, a surgical technique is provided for the use of injectable disc nucleus (IDN) as a replacement for or the augmentation of the natural nucleus pulposus. The IDN is preferably a curable biocompatible polymer with properties that emulate those of the natural human disc. A suitable IDN material is disclosed in U.S. Pat. Nos. 6,423,333; 6,033,654; and 5,817,303, which issued to Protein Polymer Technologies, Inc. The disclosures or these patents are incorporated herein by reference. These patents disclose a proteinaceous curable polymer that has physical properties close to those of the human disc nucleus pulposus and that includes certain adhesive properties that allow the polymer to adhere to the disc annulus and any remaining disc nucleus pulposus.

Figure 2:
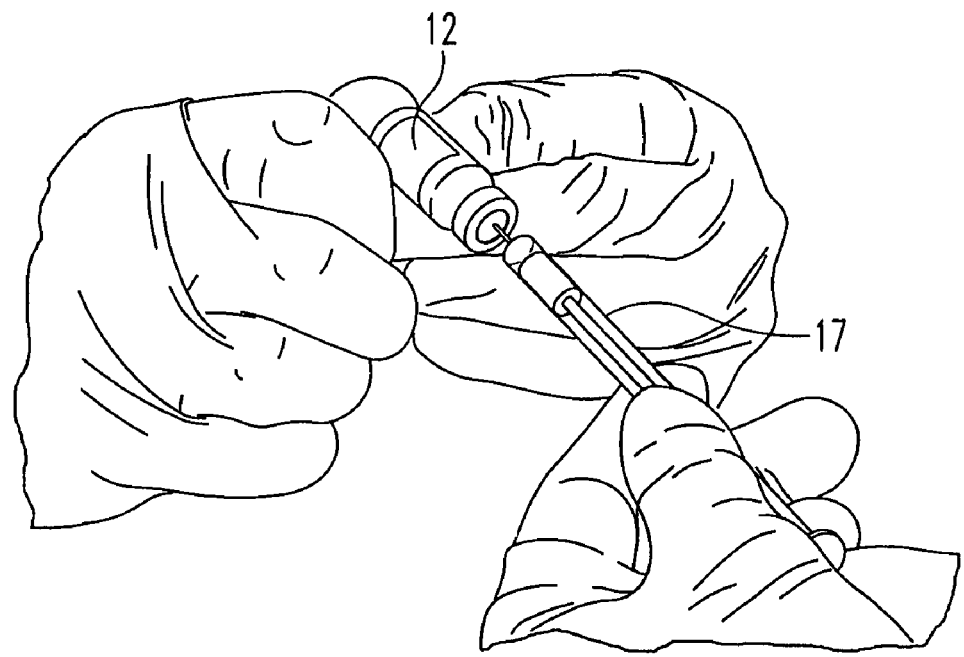
FIG. 2 is a pictorial view of the withdrawal of a cross-linker to be added to the biomaterial in the mixing system shown in FIG. 1.
Figure 3:
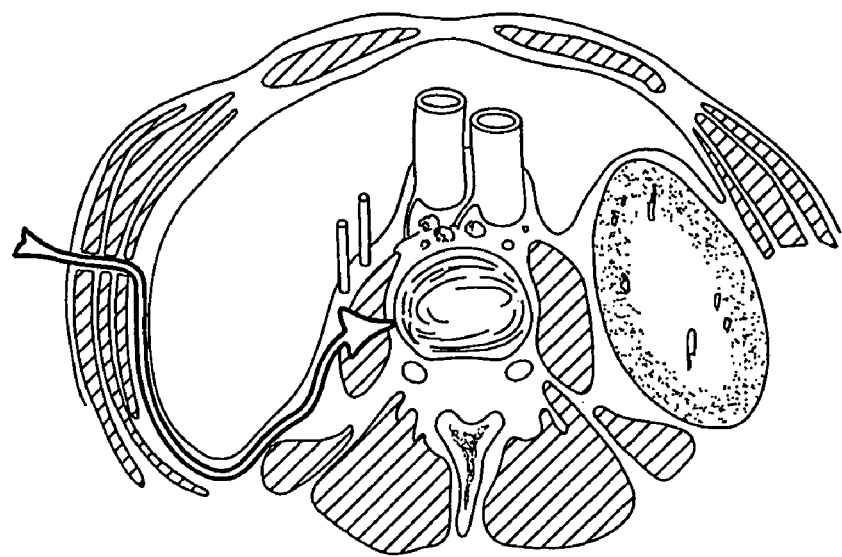
FIGS. 3-5 are diagrammatic view of surgical approaches to the intervertebral disc.
Figure 4:
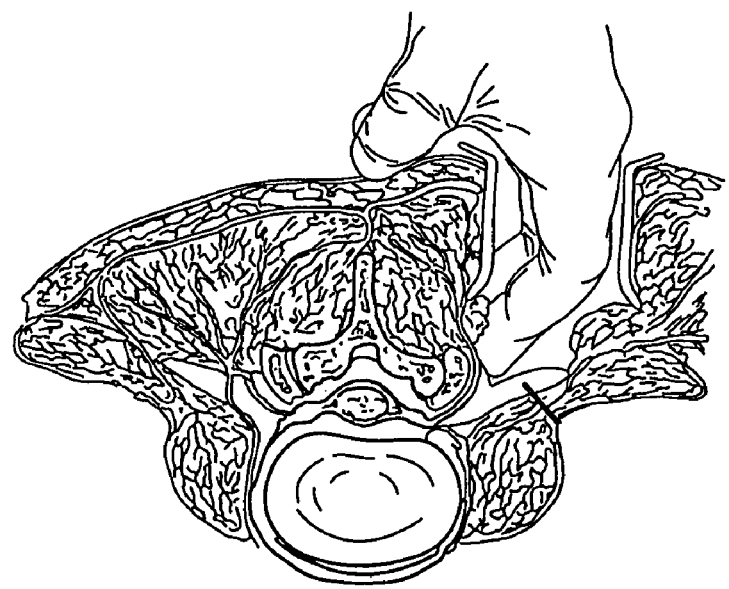
Figure 5:
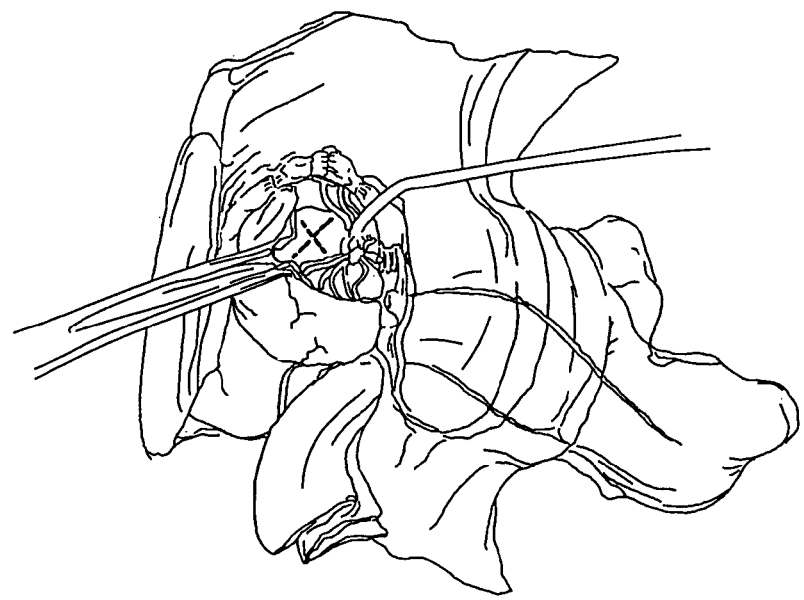

In a first step of the technique, a mixing system 10 is provided for mixing the constituents of the IDN material, as shown in FIG. 1. The mixing system 10 may be constructed as disclosed in co-pending, commonly assigned patent application Ser. No. 10/803,214, entitled "Systems and Methods for Mixing Fluids". The entire disclosure of this application is incorporated herein by reference, and particularly the discussion of the embodiment shown in FIGS. 3-9 in that application. In a specific embodiment, the mixing system 10 is prepared prior to the start of surgery by loading the assembly with four mL of a polymer constituent. This volume is mixed with a cross-linker constituent. In the specific embodiment, the volume is mixed with 34±1 µL of crosslinker drawn from a sterile vial 12 into a 100 µL syringe 14, purged of air, as shown in FIG. 2. The syringe is placed on the sterile table until it is needed for the mixing and injection step.

Where the biomaterial is an IDN, access to the intradiscal space is required. While many surgical approaches may be used, in one specific embodiment, the surgeon will use an extraforaminal mini-open approach to the disc. This may be either by a lateral retroperitoneal approach (FIG. 3) or a paramedian approach (FIG. 4) through the paraspinal muscles of the back. Access to the nucleus is gained through an extraforaminal annulotomy, so as to not expose the spinal canal or foramen to any undue risk. The annulus is identified and a minimal annulotomy is performed to gain access to the intradiscal space. If necessary, a cruciate annulotomy of up to 5 mm×5 mm may be used. The annulotomy should be oriented obliquely with one cut oriented with the outer fibers of the annulus, as shown in FIG. 5. The nucleus pulposus is then partially or completely removed using known techniques, such as using pituitary rongeurs and/or curettes. Alternatively, a mechanical method such as endoscopic shaving, hydraulic or radiofrequency (RF) technology may be used. The nucleotomy should be fully irrigated once all loose fragments have been manually removed.

Figure 6:
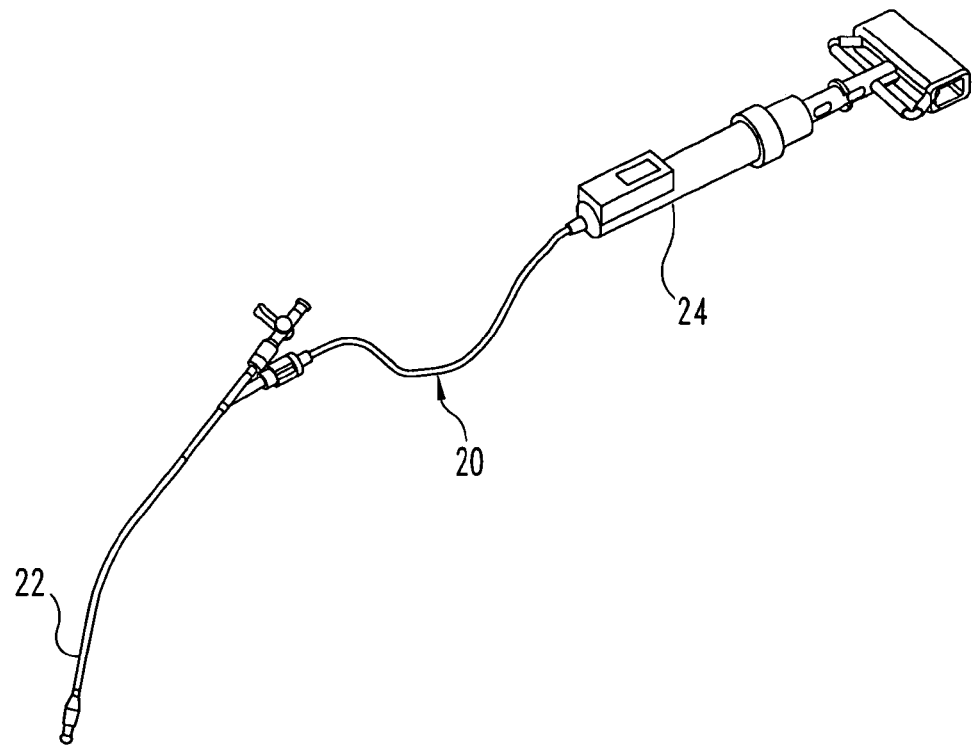
FIG. 6 is a pictorial view of a trial balloon assembly for use in a method of one embodiment of the present invention.
Figure 7:
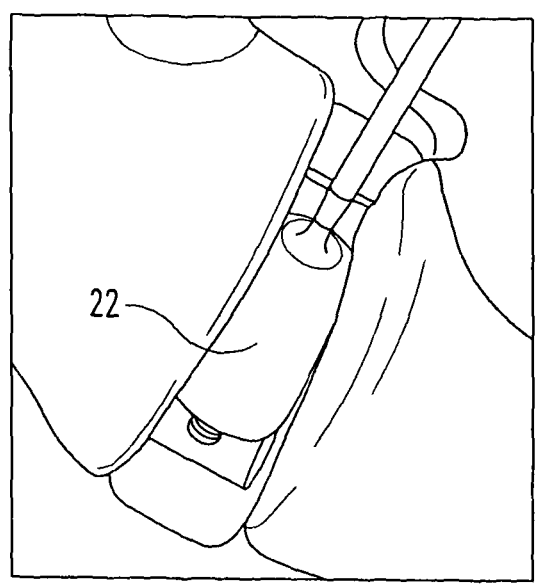
FIG. 7 is a pictorial representation of the use of the trial balloon shown in FIG. 6 in accordance with one aspect of the invention.
Figure 17:
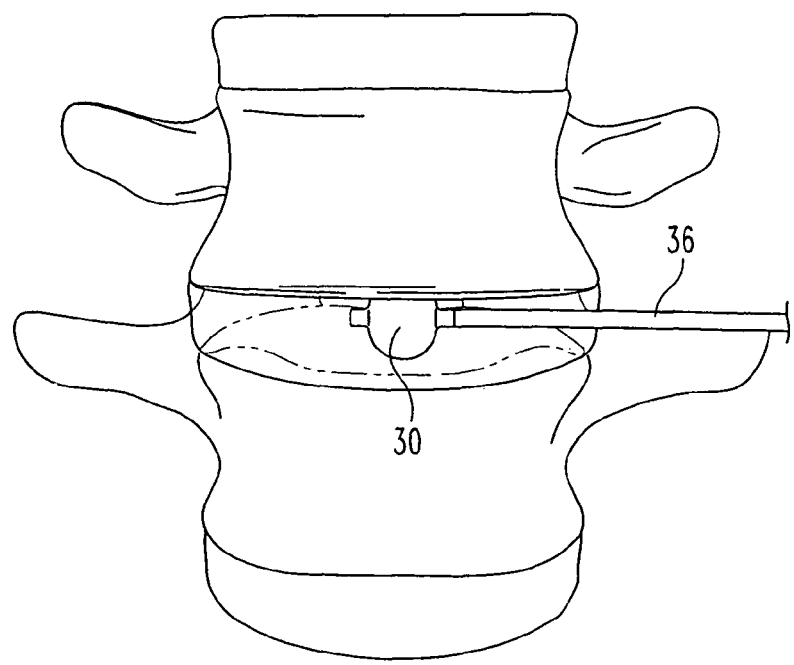
FIG. 17 is an enlarged pictorial view of the distraction balloon shown in FIG. 9.

The prepared nuclear cavity should be visualized prior to proceeding using a compliant trial balloon assembly 20, as depicted in FIG. 6. Once the balloon 22 is assembled to the inflation syringe 24 and primed with an inflation medium, the balloon is inserted through the annulotomy until it stops against the far border of the nucleotomy space. Preferably, the inflation medium is a fluid contrast medium that can be visualized under fluoroscopy. Injection of contrast media into the balloon and inflation under light pressure will allow the surgeon to judge the location and size of the space (FIGS. 7 and 17). In certain embodiments, the disc space can be visualized and the inflated size of the trial balloon measured to determine the distracted size of the disc space. An endoscopic camera may also be used to inspect the interior of the nucleotomy space, if desired by the surgeon.

If further removal of nucleus pulposus is indicated, the balloon can be removed and the nucleotomy continued. This iterative process may be repeated until the surgeon is satisfied with the size and location of the nucleotomy. In one feature of the invention, the final volume of contrast media injected into the balloon may then be used to estimate the volume of the nucleotomy and determine the amount of IDN that will be needed to fill the space.

Figure 8:
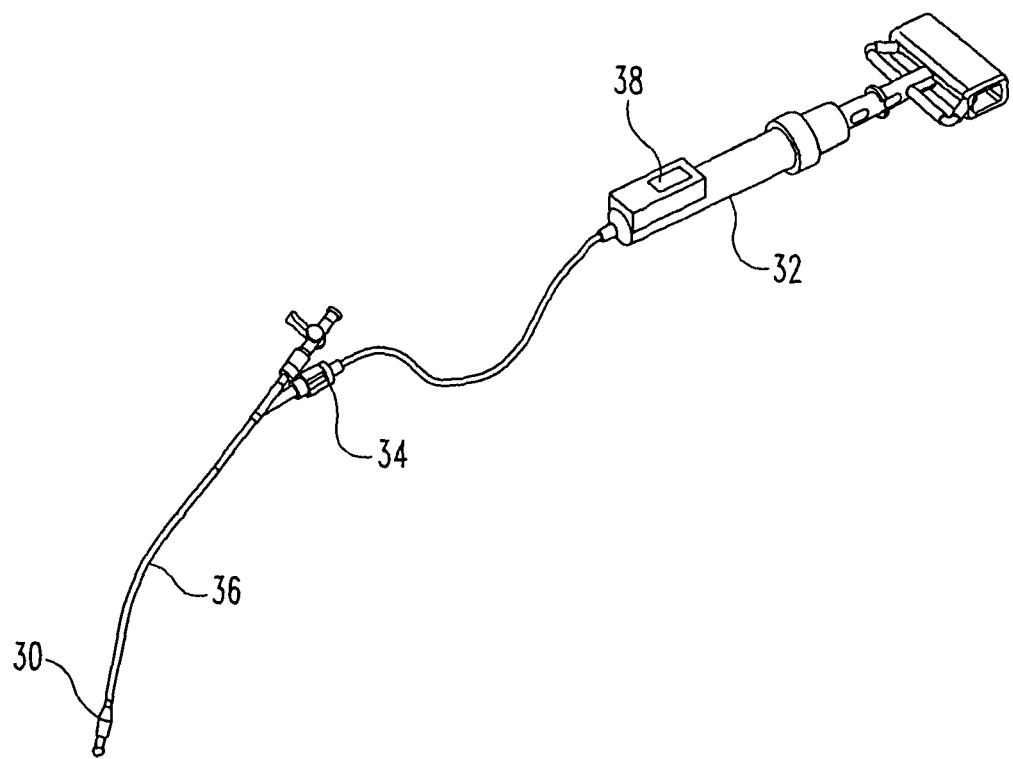
FIG. 8 is a pictorial view of a distraction balloon for use in a further aspect of the present invention.

Once the size of the space has been determined, the next step of the present invention involves distracting the space. In one embodiment, distraction of the disc is accomplished using a spherical balloon 30, such as a 15 mm diameter spherical balloon. The balloon is made of a non-compliant material and is adapted to provide a distraction force against the endplates of the disc. In a specific embodiment, the balloon 30 is able to be pressurized to approximately 13 atmospheres (200 psi). It is inflated using an inflation syringe 32 attached to the Luer fitting 34 on the catheter 36 of the balloon, as shown in FIG. 8. Pressure feedback is preferably obtained through tactile feel as the handle 35 is depressed, and/or through a pressure gage 38 mounted on the body of the inflation syringe.

Figure 9:
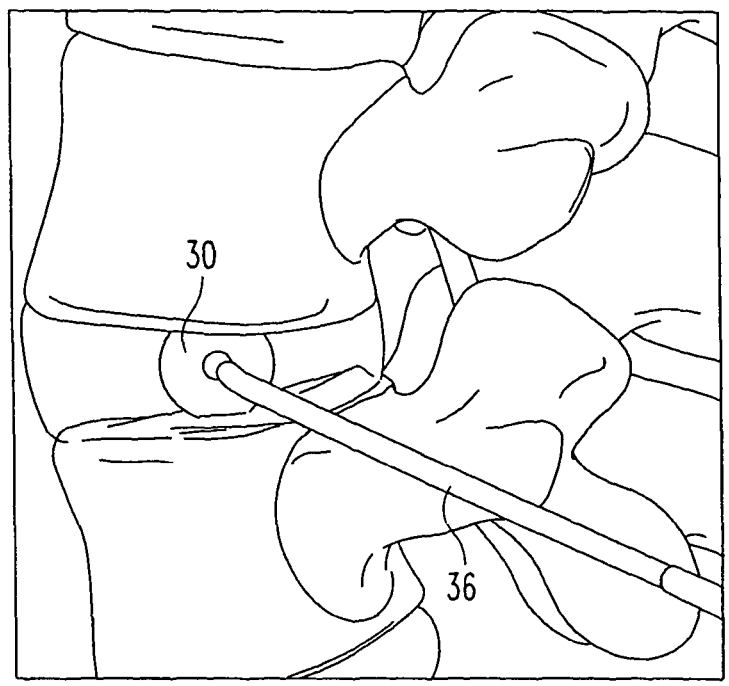
FIG. 9 is a pictorial representation of the distraction balloon of FIG. 8 shown in situ.
Figure 10:
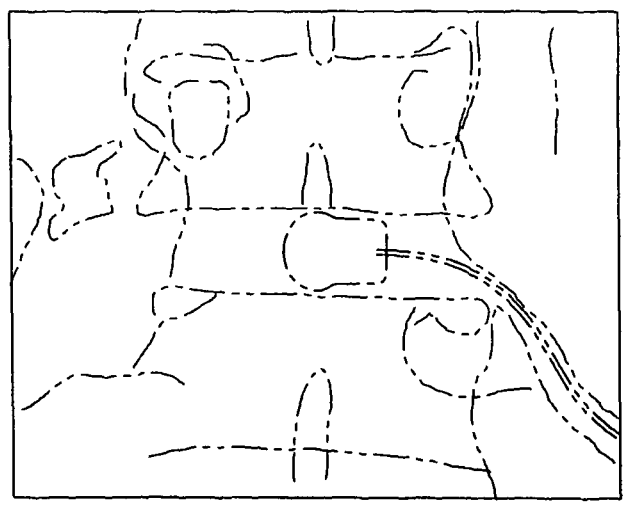
FIG. 10 is a fluoroscopic view of a distraction balloon in situ.

When the syringe and balloon are primed with contrast media, the balloon is inserted into the disc space until it stops against the far border of the nucleotomy, as shown in FIG. 9, but is preferably positioned in the center of the disc space. The balloon is gradually inflated until it contacts the endplates and ultimately pushes apart the endplates to achieve the desired amount of distraction (FIG. 10). By creating a nucleotomy that is greater in diameter than the diameter of the balloon, the surgeon can ensure that no loading of the annulus occurs and that the distraction force is applies solely to the endplates. Care should be taken to ensure the pressure rating of the balloon is not exceeded and that the endplates are not compromised by over-distraction.

Once the desired amount of distraction has been obtained, the balloon is deflated and removed from the disc. At this point, the trial balloon 22 may be used again to evaluate the resulting final nucleotomy. If the trial balloon is re-used, the resulting fluid volume may again be used to estimate the volume of IDN needed to the fill the distracted space.

Alternatively, distraction may be obtained using the surgeon's preferred technique. Other distraction techniques such as laminar distraction, screw/pin distraction, patient positioning, and traction may be used. As preservation of an intact endplate is important, the distraction technique may need to be altered from patient to patient in order to address this matter. One technique may be preferred over others in certain instances due to patient bone quality and anatomy. If additional distraction is applied, the trial balloon 22 may be used again to provide an estimate of the requisite IDN fluid volume.

In one aspect of the procedure, the distraction of the disc space is maintained by the patient's anatomy, rather than by a distraction device maintained in the disc space. It has been found that if the distraction accomplished as described above is maintained for a certain length of time the spinal ligaments will stretch and retain their lengthened configuration for sufficient time to inject the IDN and allow it to cure. In a specific embodiment, maintaining the distraction for about 5 minutes was sufficient to cause the surrounding ligaments to maintain the distraction long enough to complete the IDN injection and curing process.

Figure 11:
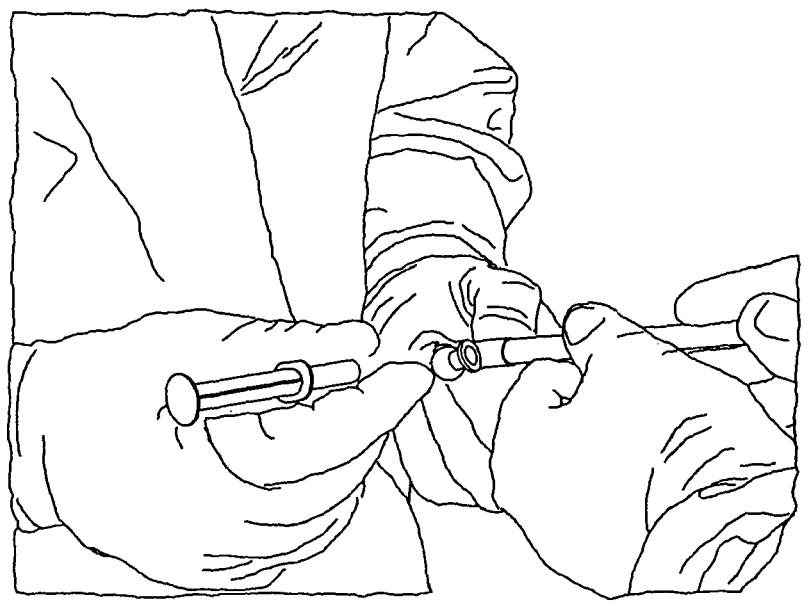
FIG. 11 is a pictorial view of the injection of the cross-linker into the biomaterial mixing system.

Immediately prior to injection, suction is applied to the cavity formed by the removal of tissue during the nucleotomy. A surgical swab may also be used to wick away excess moisture from the injection site. This will ensure that excess fluid does not interfere with the injection of the IDN material. Once the injection site has been prepared, the surgeon will hold the syringe assembly 10 with the crosslinker injection port 12 oriented upward. The entire volume of polymer should now reside in one syringe 14. The sterile assistant will inject the pre-measured volume of crosslinker from the crosslinker syringe 14 into the mixing assembly 10 through the port 12, as shown in FIG. 11.

Figure 12:
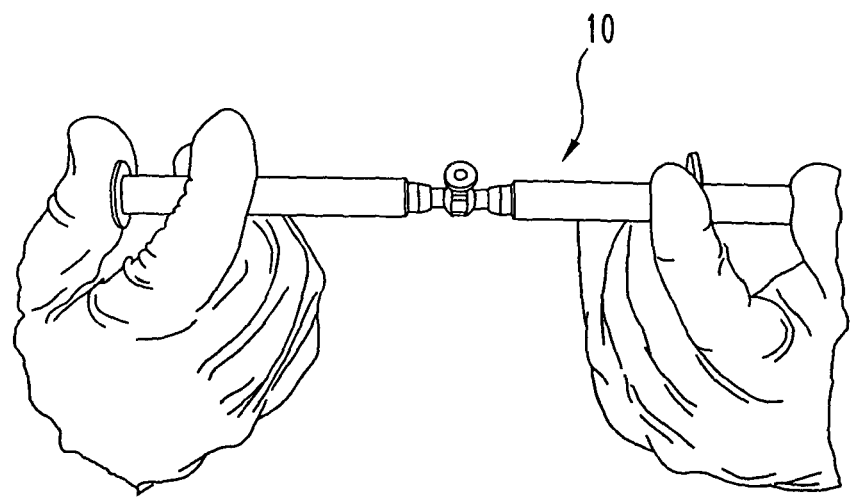
FIG. 12 is a pictorial view of the step of mixing the biomaterial within the mixing system.

The surgeon then mixes the crosslinker and polymer by cycling the plungers of the syringes 14 and 16 back and forth a predetermined number of cycles that is based upon the properties of the particular polymer. For the proteinaceous polymers disclosed in the Protein Polymer patents described above, the plungers are preferably cycled through 10 full cycles in 10 seconds (FIG. 12). For these polymers, it is important to complete the mixing procedure in ten seconds or less in order to ensure complete and proper mixing of the IDN. Upon completion of the mixing step, the surgeon disassembles the syringe 14 (no insert in the syringe) from the adapter 13. From this point, the surgeon has a fixed amount of working time to perform the injection using the second syringe 16. With the specific polymers, this working time is about 80 seconds. An appropriate previously selected injection needle is connected to the tip of the syringe 16 and the needle is primed with the fully mixed biomaterial composition prior to introducing the needle to the injection site. The initial drops from the injection needle can be ejected onto the surgical field and used as a qualitative gage of the working time of the IDN during the injection procedure.

Figure 13:
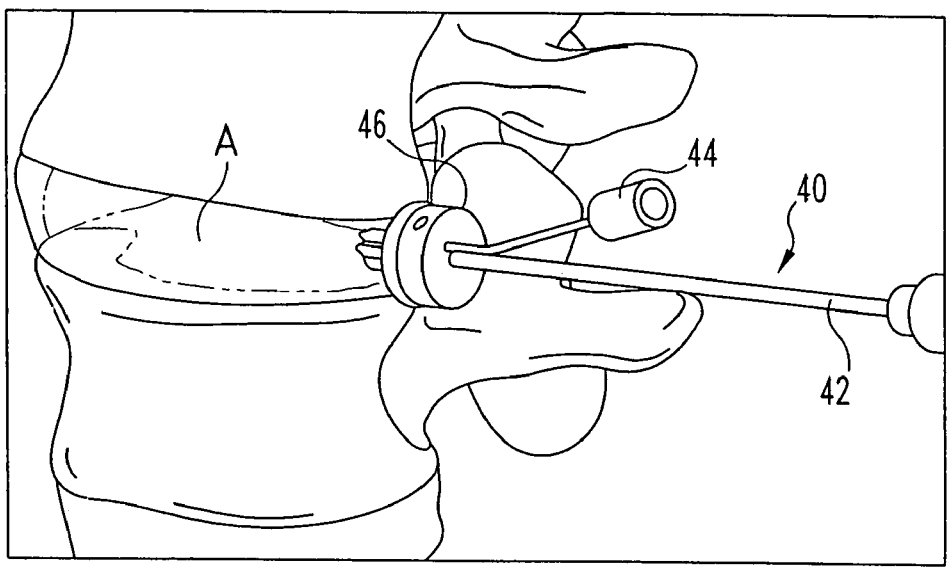
FIG. 13 is a pictorial representation of a vented injection needle assembly in accordance with one aspect of the present invention.

In accordance with one construction, the injection needle is provided as part of an injection assembly 40, as shown in FIG. 13. The injection needle 42 extends through a seal element 46 that is configured to provide an essentially fluid tight seal against the disc annulus A. A vent 44 also extends through the seal 46. The seal 46 is shown in more detail in FIG. 15. In a particular form of the construction, the seal 46 includes a body 48 that is preferably formed of a resilient material that can be compressed slightly under manual pressure to conform to the irregular external surface of the disc. The body 48 defines a sealing face 50 that bears against the disc annulus A (FIG. 13) to form the fluid tight seal.

Figure 15:
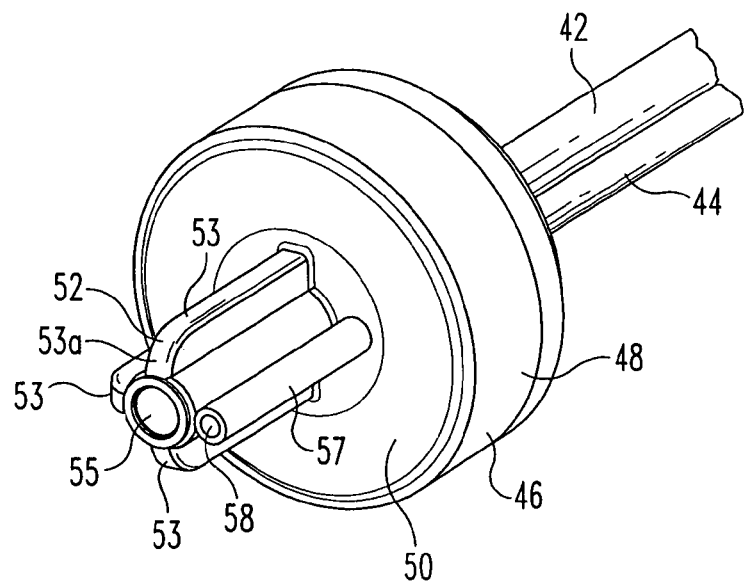
FIG. 15 is a front perspective enlarged view of the vented injection needle in accordance with one embodiment of the invention.

Extending from the sealing face 50 is an engagement boss 52. The boss 52 is preferably configured in accordance with the shape of the annulotomy cut into the annulus. As illustrated, the annulotomy is cruciate, so that boss 52 is also cruciate in shape. In particular, the boss 52 includes wings 53 that are sized to fit within corresponding legs of the cruciate cut into the annulus A. The leading edges 53a of the wings 53 can be rounded, as shown in FIG. 15, to facilitate placement of the boss 52 within the annulotomy.

The vent 44 provides an additional wing 57 for the boss 52. The wing 57 includes a channel 58 that integrates with the hollow vent 44. Preferably, the vent wing 57 is co-extensive with the other wings 52. Alternatively, the working end of the wing 57 can project slightly farther into the disc space. The injection needle 42 feeds to a channel 55 defined in the boss 52 to provide a pathway for the IDN into the disc cavity.

Figure 14:
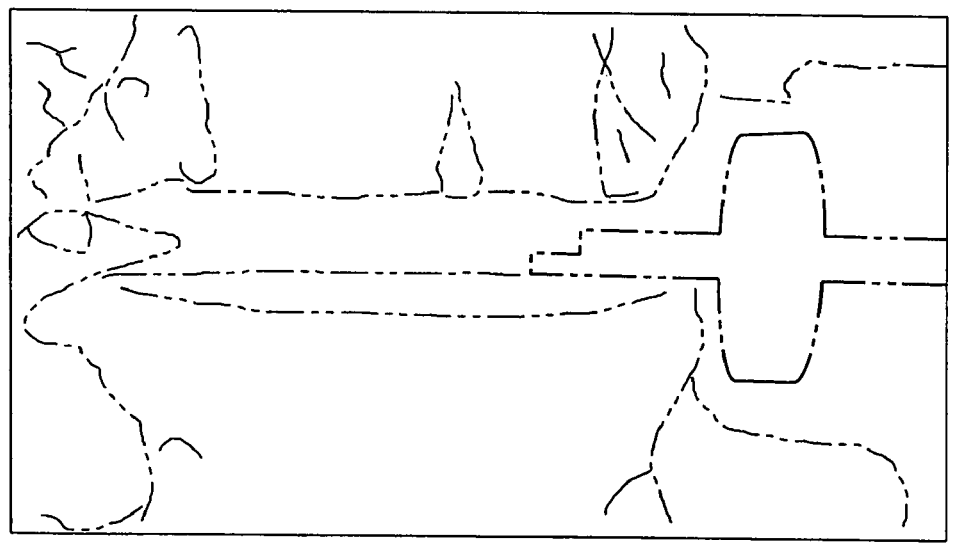
FIG. 14 is a fluoroscopic view of the vented injection needle assembly of FIG. 13 shown in situ.
Figure 16:
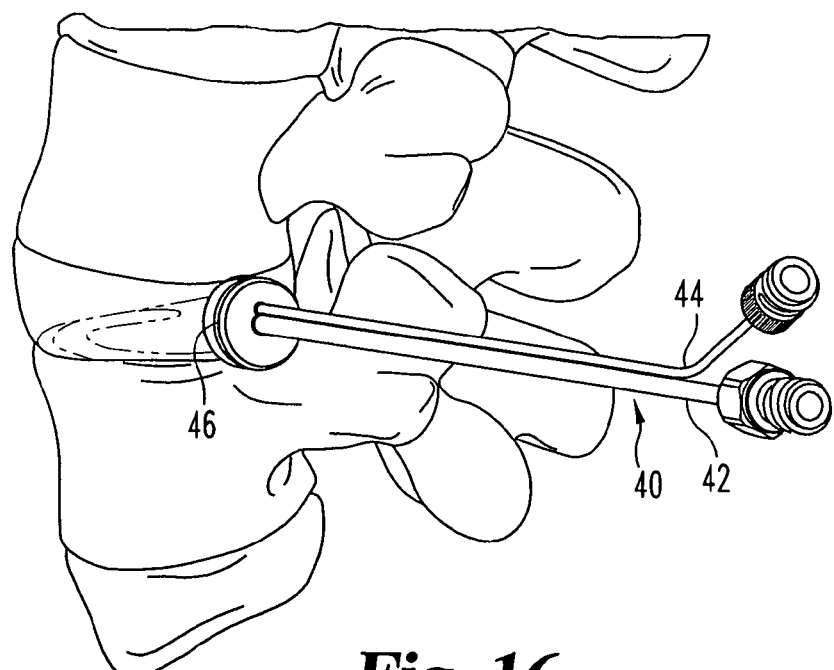
FIG. 16 is an enlarged pictorial view of the vented injection needle depicted in FIG. 15 shown in situ.

In accordance with another aspect of the procedure, the needle is introduced through the annulotomy, while carefully retracting the nerve root, until the plug seal 50 seats against the annulus, as depicted in FIGS. 13-14. Preferably, the needle is positioned so that the vent 44 is facing upward during the injection, as depicted in FIG. 16. Pressure is applied to the seal 46 to ensure no IDN leaks out between the seal and annulus. Preferably, this pressure is applied manually by the surgeon by simply pressing the needle catheter 42 toward the annulus. Since the IDN injection occurs at low pressures, the amount of force required to maintain a fluid-tight seal between the seal face 50 and the annulus is minimal.

Alternatively, the injection assembly 40 may be modified to incorporate various of the sealing techniques described in co-pending application Ser. No. 10/282,755, filed on Oct. 29, 2002 in the name of inventors Boyd et al., and assigned to the assignee of the present invention and application. This co-pending application, entitled "Devices and Methods for the Restoration of a Spinal Disc", was published on May 1, 2003, as Pub. No. US2003/0083641A1. The disclosure of this co-pending and commonly assigned patent application and publication is incorporated herein by reference for all purposes, and specifically the disclosure of the sealing and venting techniques illustrated in FIGS. 11-14 thereof.

The IDN is injected into the space until IDN is seen flowing into or out of the vent tube. In a specific embodiment, the vent tube 44 is clear so that the presence of IDN fluid within the vent can be immediately detected. At this point, the injection is stopped and the needle is held in place until the IDN takes its initial set. A microscope or loupe may be used to visualize the injection process.

As disclosed herein, the IDN is allowed to substantially completely cure before the injection needle assembly 40 is removed and the surgical site is closed. The cure period depends upon the particular IDN material. For the specific proteinaceous polymer discussed above, the cure period is a minimum of about five minutes. If IDN material is left within the annulotomy or external to the disc, it is preferably removed using rongeurs after the material has taken its initial set. Suction may also be used around the periphery of the annulotomy to remove cured material.

The volume of IDN injected into the site is preferably recorded from the graduations on the syringe 16. The injection volume will be the difference between the pre-and postinjection graduation readings. The wound is closed and dressed using the surgeon's preferred technique.

As explained above, the IDN is injected under low pressure, which at a minimum means enough pressure so that the IDN will fill all the space left by the excised nucleus material. The pressure should be sufficient so that the intradiscal cavity can be filled in an acceptable amount of time, which is determined primarily by the cure rate for the IDN. In the illustrated embodiment, the working time for the IDN (i.e., the time from complete mixing of the constituents until the IDN has cured or hardened too much to flow) is about 80 seconds. Thus, the pressure exerted through the syringe should be sufficient to completely fill the intradiscal cavity in about on minute. Manual operation of the syringe is preferred, but it is contemplated that other forms of pressurized injection of the IDN into the disc space is contemplated.

The seal 46 is formed of a resilient and deformable material so that it can be compressed against the annulus A to form a fluid tight seal. In a particular form, the seal 40 is formed of SILASTIC® or a similar elastomeric material. The seal 46 in the illustrated embodiment is cylindrical with a circular sealing face 50; however, other configurations are contemplated provided they can adequately conform to the outer surface of the disc annulus.

In a further variation, the vent 44 can simply constitute a vent opening in the seal 46. The vent tube 44 is preferred because it carries the vented fluid away from the surgical site and can bring the discharge opening within clear view of the surgeon. As a further alternative, the seal 46 can be separate from the injection needle 42 and vent tube 44. In other words, the channels 55 and 57 can extend through the body 48 of the seal 46. Catheters for the injection needle and vent can extend into the appropriate channel, preferably with a press-fit or fluid-tight engagement.

Figure 18:
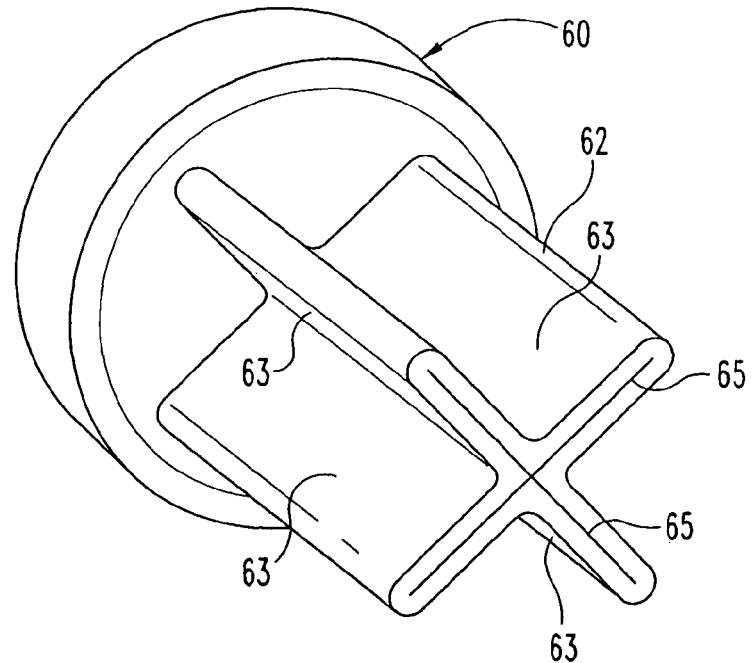
FIG. 18 is an enlarged perspective view of a seal in accordance with a further embodiment of the invention.

In yet another alternative, the cruciform boss 52 can be in the form of a duck-bill valve, as shown in FIG. 18. In particular, the seal 60 includes a valve boss 62 in the form of a cruciform duckbill valve. Each wing 63 of the boss 62 includes a slit passageway 65 that expands under fluid pressure. Thus, as fluid flows into the seal 60, the duckbill valve wings 63 expand to allow the fluid to flow into the disc space. Moreover, this expansion of the valve boss 62 enhances the seal between the cruciate boss and the annulotomy.

The procedures described heretofore are particularly well suited for open surgical procedures where a microdiscectomy is performed to remove all or a portion of the disc nucleus. One such procedure is for the treatment of degenerative disc disease (DDD) where a total or partial nucleotomy is indicated. In such an open procedure access to the spinal disc is accomplished through an incision made through the skin and subcutaneous body tissue down to the surgical site is displaced and retracted. In the case of DDD, the annulus is typically relatively intact so that a minimal annulotomy is required to gain access to the intradiscal space. It is preferred that the opening is as small as feasible to minimize damage to the annulus. In one embodiment, access can be via a K-wire over which a dilator, or a series of dilators, is passed. However, the nucleus pulposus may be significantly under-hydrated or may contain significant fissures throughout the nucleus material, producing significant patient pain and giving rise to the need for a total or substantially total discectomy.

In such a DDD procedure, in addition to the steps described hereinabove, the surgeon may also chose to perform an intraoperative step of determining the integrity of the annulus, to confirm that the annulus is competent to withstand the distraction and IDN injection pressures. To accomplish this test, upon completion of the partial or total nucleotomy and creation of an intradiscal space within the disc annulus, a saline solution may be injected into the intradiscal space through the annulotomy opening. A saline solution is preferred since it is relatively easy to aspirate for removal from the intradiscal space. However, other suitable solutions may also be used. The saline solution may be injected through a vented needle, in design and construction similar to the needle 40 shown in FIGS. 13-15. When the saline injection is under relatively low pressure (on the order of 25-40 psi under thumb pressure from the syringe and pressing the seal 46 against the external surface of the annulus), this step evaluates the integrity of the disc annulus—i.e., detects whether fissures or rents may be present in the annulus. This detection may be by tactful feel and/or by observation of leakage only at the injection needle site.

Alternatively, or additionally, the injected saline solution may be used to estimate the volume of the disc space to be filled with IDN material. If preferred, a trial balloon, such as the trial balloon 22 described above, may be used to ascertain the volume of the intradiscal space to be filled. After the annulus integrity and volume tests have been completed, suction is applied to aspirate the nuclear cavity and a surgical swab may be used to wick away excess moisture that may interfere with the injection of the IDN material. Thereafter, the surgeon may use the distraction balloon as illustrated in FIGS. 8-10 to apply a distraction force within the intradiscal space to distract the opposing vertebral bodies on either side of the intradiscal space, further separating apart such vertebral bodies. A subsequent saline test may be conducted to further verify the integrity of the annulus. The IDN may then be sealably injected under pressure using the vented needle 40 as described hereinabove. Such injection of IDN is preferred to be at a pressure that is not greater than the pressure under which the saline solution is injected and is typically on the order of 25-40 psi. While the saline solution has been described as preferably being injected with a vented needle such as described herein, it should be appreciated that a needle without a vent, but with a sealing element, could also be used in the practice of the annulus integrity test.

The methods and devices of the present invention are also contemplated for use in performing other open surgical procedures, such as an adjunct to microdiscectomy (AMD) procedure. An AMD procedure is indicated where a total discectomy is not required, or more particularly where only a partial discectomy is necessary to restore normal or near normal function to the affected disc. In a typical case, the affected disc has a herniation or tear in the disc annulus. Access to the intradiscal space is thus available through the tear in the annulus.

Prior to the start of the surgery, the injectable curable polymer constituents are pre-loaded into the mixing syringe assembly, as described above, and left on the sterile instrument table until the appropriate time for injection of the IDN material. The surgeon uses a traditional open or microdiscectomy technique of preference for access to the disc herniation site. Typically, the patient will be placed on a laminectomy frame in the prone position with the spine flexed to aid intraoperative exposure. The ligamentum flavum and laminar edge are identified. A hemilaminectomy/medial facetectomy may be performed as necessary, with the aid of lateral fluoroscopy. Exposure of the hernia proceeds in a known manner, taking care to protect the dura and nerve root. The epidural space is explored to ensure that all disc fragments have been identified.

Once the disc herniation has been identified, a determination is made as to whether a further annulotomy is needed for improved access. If so, an annulotomy may be performed as described above. The herniated disc tissue is then removed according to known techniques, such as using pituitary rongeurs and/or curettes. Laminar distraction and/or flexion of the hips can be used to aid in exposure of the hernia site. In addition, distraction of the affected disc may be desired to improve the stability of the disc. This distraction may be accomplished using any of the techniques described above. If sufficient disc tissue has been removed around the herniation site, the distraction balloon may be used, provided that the balloon is removed once the desired distraction has been achieved.

This balloon distraction may also be supplemented in a two stage distraction technique described as follows. After a total or partial nucleotomy has been performed, in the first stage, a distraction balloon, such as the balloon 30 described above, is inserted into the intradiscal space. The balloon is then inflated to gain distraction of the anterior column of the disc space.

In the second stage, a secondary distraction instrument is introduced to act on any posterior bony structures at the particular intervertebral level in accordance with known surgical techniques. The secondary instrument is used to obtain distraction of the posterior column at an appropriate amount decided by the surgeon. The nature and amount of this second stage distraction may increase the overall amount of distraction of the total space, change the lordotic angle at the intervertebral level or cause no appreciable increase in the overall distraction of the space.

Once the appropriate amount and type of secondary distraction has been obtained, the first stage distraction balloon is removed, while the secondary instrument remains in place to prevent any loss of distraction that may occur. With the distraction balloon removed, the IDN may be injected as described above. One benefit of this two-stage distraction technique is that the IDN material need not be injected under pressure in order to regain any distraction loss that may occur with the single stage distraction approaches discussed above. This benefit makes this two-stage approach particularly well suited for microdiscectomy in herniated nucleus pulposus cases in which the size of the opening or tear in the annulus can be widely variable. In these cases, sealing of the annular opening may be problematic, which ultimately makes pressurization of the IDN injection difficult.

In accordance with this embodiment, the secondary distraction instrument is preferably a laminar or interspinous instrument. A laminar distractor applies distraction force across the superior and inferior laminar arches, while the interspinous instrument applies force against the superior and inferior spinous processes. In either case, the secondary instrument does not interfere with the removal of the first stage distraction balloon or the injection of the IDN material into the distracted space.

After suitable distraction is achieved, a saline solution as described above with respect to the DDD procedure may be injected through a vented needle into the intradiscal space to check the integrity of the annulus and to determine that there are no other leakage paths, as well as to estimate the volume of the intradiscal space to be filled. While this annulus integrity test is described as being conducted after distraction, it may also be done after removal of nucleus and prior to distraction.

When the nuclear cavity has been prepared, the surgeon mixes the IDN constituents, as described above, to prepare the IDN material for injection. An injection needle, which is not required to be a vented, sealed needle, is introduced through the opening in the annulus until the needle tip reaches the far side of the cavity. As the IDN material is injected, the needle is preferably angled side-to-side and gradually withdrawn toward the annulus to ensure a complete fill of the space. When the IDN material is detected at the inner border of the annulus opening, the injection is stopped and the needle is removed from the site. Alternatively, a vented needle 40 with a seal 46 may be used, such as where the rent through the annulus is relatively small and not too irregular. With a vented needle 40, the injection is stopped when the IDN material is seen at the vent. It is contemplated that the IDN material will be injected under pressure, typically on the order of 25-40 psi, to ensure complete fill of the cavity, with the seal 46 of the vented needle 40 being pressed against the annulus during IDN injection.

The present invention also contemplates a procedure for percutaneous direct injection of a curable biomaterial for treatment of degenerative disc disease. As explained above, treatment for DDD is indicated where the disc annulus is generally intact, but the nucleus pulposus has been compromised, either by dehydration or the creation of fissures and the patient suffers from significant pain. In some DDD procedures, for example, as described hereinabove, some or all of the nucleus is removed to create an intradiscal space for injection of curable biomaterial. In accordance with the following descriptions of the invention, the defective or degenerated nucleus is not removed, but is instead augmented by a curable biomaterial or IDN material in a percutaneous procedure.

In a percutaneous procedure as intended herein, access to the spinal disc is achieved simply by introduction of a relatively small and sharp cannulated device, which may include a needle, through the skin and body tissue down to the surgical site under fluoroscopy or by using other conventional surgical navigation techniques. No incision is made nor is any body tissue retracted. Further, injection is continued by insertion of the cannulated device through the annulus into the nucleus pulposus, preferably without additional dilators and without removing any of the annulus tissue. As such, the percutaneous procedure of the present invention provides a minimally invasive approach to treating DDD conditions.

A first step of the procedure is preferably to obtain a pre-operative discogram. The discogram will verify whether the annulus has sufficient integrity and competency to contain the injected nucleus augmentation. Ordinarily, the discogram will be performed two or three days prior to the comprehensive surgery. As explained in more detail below, since the IDN material is preferably injected at a relatively high pressure, verification of annulus integrity is desirable. The pressure of the injected IDN is preferably at least as high as 100 psi and potentially as high as 200 psi so as to achieve distraction of the opposed vertebral bodies and increased disc height, desirably approaching normal anatomical conditions, upon injection of the IDN. In this discogram, the patient may be given an epidural injection and an inflation syringe is used to inject a contrast solution directly into the disc. The inflation syringe 32 shown in FIG. 8 may be used to introduce the pressurized contrast medium. For this procedure, the inflation syringe 36 is modified to eliminate the balloon 30 mounted to the end of the catheter 36, leaving the lumen of the catheter open for the contrast medium to flow through into the disc. The pressure gage 38 may be used to verify the fluid pressure as the contrast agent is manually injected into the disc. Preferably, the injection pressure for the contrast medium is established by correlating its viscosity relative to the viscosity of the IDN material to be injected. If the viscosity is generally the same, the injection pressure for the IDN should not be greater than the pressure of the injected contrast medium in the discogram. In a specific embodiment, the contrast medium is injected to approximately 160 psi. If the contrast medium has a lesser viscosity than the IDN, the injection pressure of the injected contrast medium may be decreased accordingly, so as to lessen the pain the patient may experience. If leakage is observed under fluoroscopy, use of the direct injection of IDN may be contraindicated and alternative treatments may be sought, one of which is described hereinbelow.

The discogram procedure is conducted in accordance with conventional techniques as shown and described, for example, in U.S. Pat. No. 6,370,420, which is incorporated herein by reference. While the contrast medium used in the discogram is fluid it is typically viscous, approximating the viscosity of the pre-cured IDN material. In addition, it has a contrast agent that allows it to be visualized under fluoroscopy or other imaging techniques, permitting a visual observation of any leakage paths or fissures in the disc annulus prior to surgery. A discogram is commonly done several days prior to surgery so as to allow the contrast medium to dissipate and be absorbed into body tissue. However, an intraoperative discogram may also be considered.

As another possible intra-operative test of annulus integrity, a saline solution as described hereinabove may be considered. While a saline solution may be easier to remove than contrast medium, there is not sufficient contrast agent for fluoroscopic visualization or like imaging. Leaks may be detected manually, however, by tactile sensing by the surgeon, especially if upon injection of the saline solution pressure fails to build and stop, with injection of saline injection continuing. As such, a saline solution test may be performed intra-operatively as a final annulus integrity test as well as for determining the approximate volume of IDN material to inject.

Figure 19:
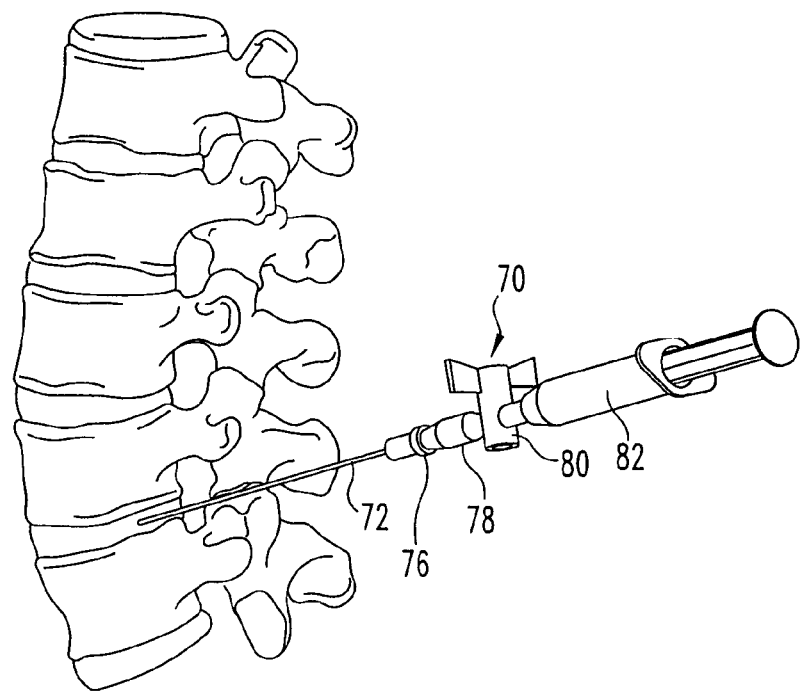
FIG. 19 is a lateral pictorial view of the spine with an injection assembly positioned to introduce a curable biomaterial into an affected disc in a percutaneous procedure.
Figure 20:
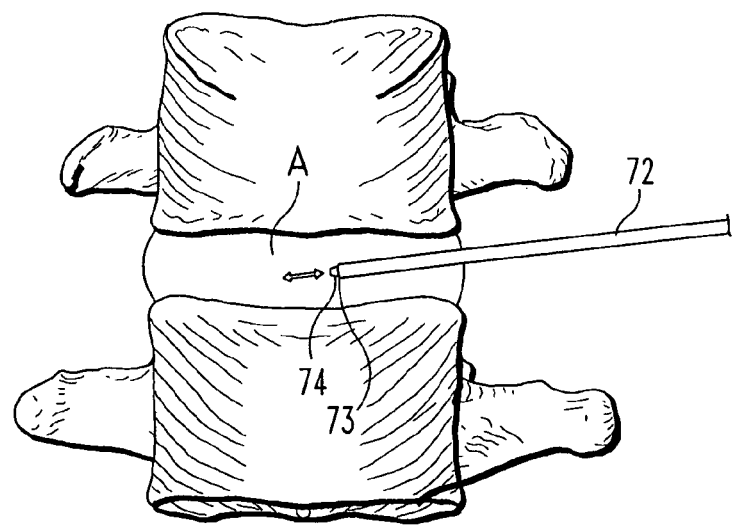
FIG. 20 is an enlarged view of the disc shown in FIG. 19 with the injection needle and docking cannula of the injection assembly positioned within the disc annulus.

In accordance with the percutaneous procedure, the IDN material is prepared in the same manner described above, with the loaded mixing assembly and crosslinker syringes made available on a sterile instrument table until the appropriate time for injection of the IDN material. In particular, the injection assembly 70 shown in FIGS. 19-20 is used to accomplish the injection step. The assembly 70 includes a sharp cannulated device, such as a thin-walled docking cannula 72 with an integral mating hub 76. In this particular construction, the cannula 72 has an relatively smooth outer surface and substantially constant outer and inner diameters along its length. An injection needle 74 (FIG. 20) is slidably disposed within the docking cannula in a relatively close dimensional fit. The needle 74 is integral with a hub 78 that may be configured to mate with the hub 76 of the cannula. A stopcock valve 80 is fluidly connected to the hub 78, and the injection syringe 82 is configured to engage the stopcock valve in any known manner effective to create a fluid tight connection. The injection syringe 82 may be one of the syringes 14, 16 of the mixing system illustrated in FIG. 1.

The patient is preferably placed in a prone position on an appropriate conventional Andrews frame or equivalent table, in the proper lordotic posture with the hips flexed to aid in the exposure of the posterior disc. The docking cannula 72 is introduced to the disc in an extraforaminal location using a typical posterolateral discography approach. A guide stylet may extend through and be disposed in the cannula to assist in passing the cannula through the body tissue to the disc annulus A. The tip of the docking cannula 72 is preferably confirmed, via fluoroscopy, to reside within the disc annulus, as depicted in FIG. 20. The stylet is removed once the docking of the cannula 72 is achieved. However, it is essential that the tip of the docking cannula break through the annulus into the nucleus pulposus to ensure injection of the IDN material into the nuclear space and not into the annulus. In this initial step of the surgical procedure, the docking cannula 72 will be engaged in the annulus and the hub 76 supported by the soft tissue between the disc and the entry point in the patient's back. The docking cannula is therefor sized for percutaneous introduction, while sufficiently large to accommodate an injection needle capable of injecting the IDN material. Thus, in a specific embodiment, the docking cannula may be a 16-20 hypodermic gage cannula. The cannula has a length from the tip 73 to the hub 76 that is sufficient to allow the hub to sit outside the body. In a specific embodiment, the docking cannula 72 has a length of about 100 mm.

While a sharp-tipped stylet may be used in a conventional manner to aid insertion of the docking cannula, the docking cannula 72 itself may be configured to puncture the disc annulus, such as by a sharpened edge at the tip 73 of the cannula. Once the docking cannula is properly docked within the annulus it forms a substantially fluid-tight interface with the disc annulus. Since the procedure does not require an annulotomy, the elasticity of the annulus and other tissues surrounding the disc cause those tissues to compress around the cannula 72 to effect a seal. In addition, the injection needle 74 is sized for a close running fit within the docking cannula 72. Preferably, the injection needle is no more than two gages smaller than the docking cannula. Thus, in the specific example, the injection needle may be 18-22 hypodermic gage corresponding to the 16-20 hypodermic gage cannula dimension.

Once the cannula 72 has been docked within the annular wall the IDN may be prepared as described above with reference to FIGS. 11-12. The IDN material may be the proteinaceous polymer that is the subject of the Protein Polymer Technology patents discussed above. The proteinaceous polymer in those patents is described as having a lap shear tensile strength that within 30 minutes, usually within 15 minutes, more usually within 5 minutes, will be at least 100, preferably at least about 250, more preferably at least about 300, usually not exceeding about 4000, more usually not exceeding about 3000 g/cm$^2$. This polymer is particularly well-suited for the percutaneous DDD procedure because as a result of its strong adhesive properties the polymer adheres to the existing nucleus pulposus and disc annulus. It is also biocompatible and permeable, containing about 80% water. As described in more detail below, the IDN material is injected under pressure into the nucleus pulposus to fill all voids, interstices and fissures that may exist in the existing nucleus. When the polymer cures in situ, it adheres to the existing natural disc material for essentially seamless integration with the existing disc nucleus, thereby substantially restoring the normal disc function. Further, since the IDN is injected directly into the nucleus within the disc space without any balloon or other physical barrier, there is greater potential for transporting nutrients to the cells and vertebral endplates surrounding it.

Once the IDN material has been prepared within the syringe 82, the syringe is mated with the stopcock valve 80 of the injection needle hub 78. The injection needle is then fed into the docking cannula 72 and into the nucleus pulposus and extended approximately to the center of the disc. The position of the needle tip is preferably confirmed via fluoroscopic imaging. The entire IDN injection process should be completed fairly rapidly before the IDN material cures to a viscosity that will prevent full introduction of the IDN into the entire disc nucleus. In the specific embodiment using the polymer material discussed above, the surgeon must complete the injection within about 80 seconds after the IDN material has been fully mixed. Proper placement of the docking cannula 72 and the mating fit between the cannula hub 76 and the injection needle hub 78 can ensure that the needle tip is positioned substantially at the center of the disc, so that the fluoroscopic verification can be completed very quickly.

Once the needle tip position is verified, the syringe 82 may be manipulated to inject the IDN material through the needle 74 and into the disc space. Again, given the curing time constraints, the injection must proceed smoothly but rapidly so that all of the IDN material is injected into the disc space under pressure. In one embodiment, the IDN material is injected at a pressure in the range of about 100-160 psi, which is considered sufficient to achieve some distraction of the disc to account for some disc compression that may be associated with the DDD condition. This will provide increased stability to the disc, thus treating pain associated with DDD conditions. Since the present procedure is percutaneous, no initial pre-distraction of the disc space is accomplished beyond the amount of distraction that can be obtained by proper positioning of the patient on the Andrews frame.

The injection pressure may be estimated by the amount of manual pressure that can be achieved with the injection syringe 82. Alternatively, a pressure gage may be mounted to the needle hub 78 or stopcock valve 80 to provide a visual reading of the injection pressure. It is understood that the pressurized IDN material will seek to fill all voids and fissures in the disc nucleus pulposus, but will be contained by the disc annulus.

Once the desired amount of IDN material has been injected, the stopcock valve 80 is closed to maintain the fluid pressure. The injection assembly 70 is preferably held in place during the minimum cure time, which is about five minutes in the specific embodiment. After the initial cure period, the injection needle is removed. The natural disc and augmenting IDN material will collapse to fill the minimal channel left by removal of the injection needle 74. The quick curing of the material, coupled with its natural adherent properties allow the IDN to substantially fully seal the entry point into the disc nucleus. The percutaneous nature of the procedure allows the wall of the disc annulus to collapse around the minimal channel left after the docking cannula 72 has been removed from the disc.

In a particular practice of the injection step, the injection needle 74 may be gradually retracted as the IDN material continues to be injected. Careful and controlled movement of the syringe 82 is necessary to ensure that the injection needle is retracted only to the inner border of the disc annulus and maintained in that position during the initial cure period. With this practice, the entire disc space is substantially filled, under pressure, with the IDN material.

While the injection assembly 70 has been described herein as including the docking cannula 72 and a separate injection needle 74, it should be understood that other injection alternatives are contemplated. For example, in certain situations where perhaps the surgeon has more time to inject a curable material than the particular embodiments described, the needle 74 itself may be directly injected without use of the docking cannula 72.

Figure 21:
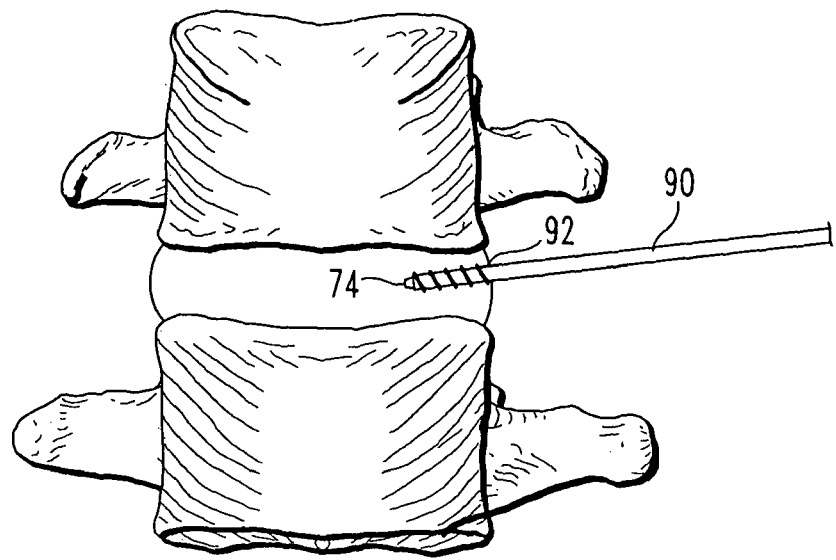
FIG. 21 is an enlarged view of a disc with a docking cannula according to a further embodiment with the injection needle extending therethrough into the disc space.
Figure 22:
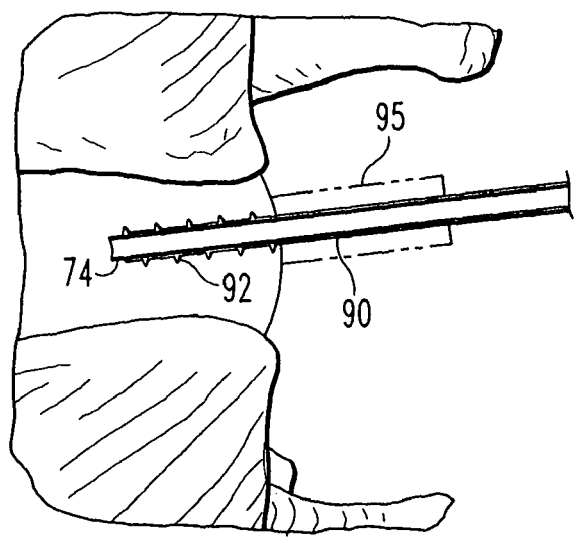
FIG. 22 is an enlarged cross-sectional view of the docking cannula and injection needle depicted in FIG. 21.

In an alternative embodiment depicted in FIGS. 21-22, a docking cannula 90 may be provided that includes a threaded tip 92. The threads are configured to pierce the annulus as the docking cannula 90 is rotated. With this alternative, the hub may be modified from the hub 76 of the cannula 72 to provide a gripping surface suitable for manual threading of the cannula 90 into the disc annulus. Such threaded cannula 90 would provide a more positive anchoring of the cannula 90 to the annulus. In addition, a seal would be provided between the threaded tip 92 and the wall of the annulus since the cannula 90 is threaded into the annulus without an annulotomy being performed. As such, it is considered that such a threaded cannula 90 would allow injection of curable biomaterial at pressures greater than 160 psi and potentially up to as high as 200 psi. To aid in the insertion of the threaded cannula 90, a thin-walled retractable outer sheath may be positioned over the threads during insertion, and withdrawn upon insertion as the threaded tip 92 nears the annulus wall. It should also be understood that as noted above, the needle itself may be used without an outer cannula, and in such a situation, the needle 74 may be provided with threads at its distal tip.

In a modification of the threaded docking cannula 90, a flange 95 may be defined on the cannula, as depicted in phantom lines in FIG. 22. This flange 95 may act as a stop to control the amount of insertion of the threaded tip 92 into the disc annulus. The flange may also assist in providing and maintaining a fluid-tight seal at the opening formed in the annulus. The flange may also include a fitting, such as a Luer lock fitting, to mate with the hub 78 of the injection needle. In this case, the fitting is preferably sized so that the fitting is accessible outside the percutaneous wound in the patient. Such a flanged cannula may have particular application in the open DDD and/or AMD surgical procedures described hereinabove.

Figure 23A:
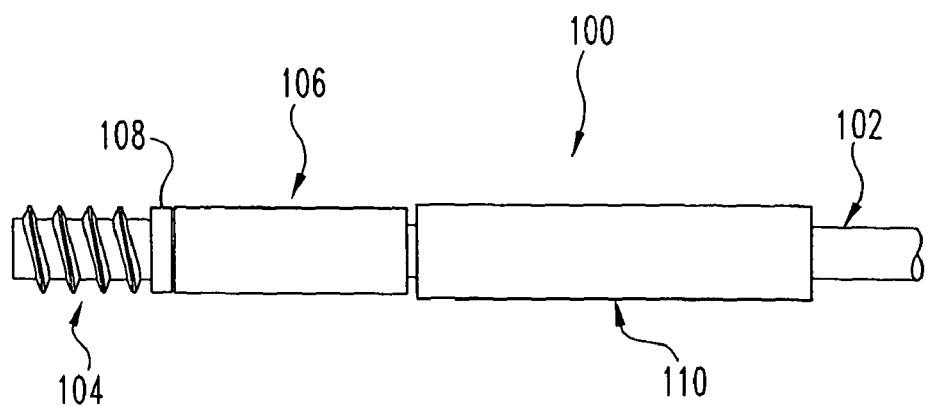
FIGS. 23a-b are side views of a docking cannula according to a further embodiment of the invention that includes an expandable flange, shown with the flange in its non-expanded and expanded positions.
Figure 23B:
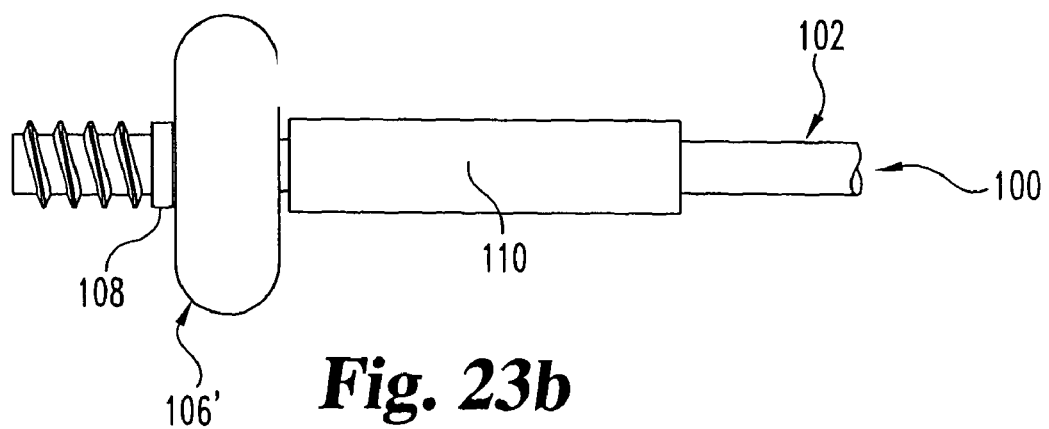

In a further modification, a threaded docking cannula 100, depicted in FIGS. 23*a-b*, includes an expandable flange 106. The cannula includes a cannula body 102 terminating in threads 104 for engagement within the disc annulus, as with the embodiments described above. The expandable flange 106 is interposed between a fixed collar 108 and a sleeve 110 that is slidably disposed about the cannula body 102. The expandable flange is configured to have an un-expanded condition 106, as shown in FIG. 23*a* and then to move to an expanded condition 106', shown in FIG. 23*b*, upon pressure from the sleeve 110. In a specific embodiment, the flange 106 is formed of a resilient material that deforms when pressed by the sleeve but returns substantially to its un-expended condition (FIG. 23*a*) when the pressure is removed. In its un-expanded condition, the flange 106 has a small enough outer profile or diameter to be used percutaneously.

As set forth above, in the percutaneous procedure for treating the DDD condition, a discogram is described as pre-operatively testing integrity of the disc annulus to determine if the disc is competent for subsequent direct injection of biomaterial under relatively high pressures of about 100 psi or more. If the discogram is negative, such direct injection is typically contraindicated. The following dual injection procedure may be considered as an alternative treatment in such situation, where the annulus is still relatively intact.

In a first step of this alternative, dual injection method, a first suitable quantity of IDN is prepared as described above and injected into the nucleus pulposus using, for example, the injection needle assembly 70 illustrated in FIGS. 19-20. The material is injected at relatively low pressure, i.e., on the order of about 25-40 psi, sufficient to allow the material to flow through and fill any fissures in the nucleus pulposus, but without causing distraction. The IDN material is allowed to cure as described above, thereby providing a seal interiorly of the annulus within the disc space. In the second step, a second suitable quantity of IDN is prepared and injected through the same access as the first injection, again using, for example an injection needle assembly 70. The second quantity of IDN is injected under relatively high pressure, on the order of at least 100 psi in order to substantially fill the disc space and distract the opposing vertebral bodies, the first cured quantity of IDN serving as a barrier to maintain the second pressured quantity of IDN with the disc space.

It should also be appreciated that a kit of the components described herein may be provided to a surgeon in order to perform the surgical procedures described herein. Thus, a kit may include, but not be limited to, a vented needle or needle assembly, a suitable quantity of IDN material or its constituent parts to be mixed, a mixer for mixing the constituent parts, and a suitable syringe.

While the invention has been illustrated and described in detail in the drawings and foregoing description, the same should be considered as illustrative and not restrictive in character. For example, while the injection assembly having either the smooth or the threaded cannula has been described as having particular application in a high pressure, percutaneous procedure, it should be appreciated that such an injection needle assembly may also be used in applications where distraction and high pressures are not warranted. It is understood that only the preferred embodiments have been presented and that all changes, modifications and further applications that come within the spirit of the invention are desired to be protected.

What is claimed is:

1. A kit of parts for use in treating a damaged or diseased spinal disc having an outer annulus and an inner nucleus pulposus, comprising:
    a cannula having a distal end, a proximal end and an inner opening extending therethrough, the distal end of said cannula adapted to be inserted through said disc annulus;
    a sharp-tipped stylet configured to fit within said inner opening and adapted to be removed from said cannula after insertion of said cannula through said annulus;
    an injection needle having a distal end and a proximal end, said distal end adapted to be inserted into said proximal end of said cannula and configured for relatively close sliding fit therewithin, said injection needle having a length sufficient so that said distal end is disposed inside the disc annulus when the needle is inserted into said cannula;
    a syringe for containing a quantity of curable biomaterial, said syringe adapted to be coupled to the proximal end of said needle and to inject said biomaterial into said needle under pressure; and
    a quantity of curable biomaterial that upon curing emulates the properties of natural nucleus pulposus.

2. The kit of claim 1, wherein said needle has a relatively smooth outer surface and a substantially constant outer diameter over its length.

3. The kit of claim 2, wherein said cannula is thin-walled, having a substantially constant outer diameter, and said inner opening extending therethrough is of substantially constant inner diameter.

4. The kit of claim 3, wherein said cannula inner diameter is sized for a close sliding fit with the outer diameter of said needle.

5. The kit of claim 4, wherein said cannula has a smooth outer surface.

6. The kit of claim 1, wherein said cannula is in the range of 16-20 hypodermic gage.

7. The kit of claim 6, wherein said needle is in the range of 18-22 hypodermic gage.

8. The kit of claim 1, wherein said cannula has a predetermined length from its distal end which is adapted to pierce through said annulus and its proximal end which is adapted to receive said needle.

9. The kit of claim 8, wherein said predetermined length is selected to allow the proximal end of said cannula to reside outside the body of a patient when the distal end extends through said annulus.

10. The kit of claim 1, wherein said cannula has an anchor portion for docking said cannula to said annulus.

11. The kit of claim 10, wherein said anchor portion comprises threads on the outer surface of said cannula along an extent of said cannula at its distal end for threadably engaging said disc annulus.

12. The kit of claim 11, further including a flange disposed on said cannula adjacent said threads, said flange being sized and configured to contact the outer surface of said annulus when said cannula is docked thereto for providing and maintaining a seal between said annulus and said flange.

13. The kit of claim 12, wherein said flange is expandable from a first dimension to a larger second dimension sized to contact the outer surface of said annulus.

14. The kit of claim 13, wherein said flange includes an elastomeric sleeve mounted on said cannula and configured to expand from said first dimension to said second dimension upon application of a force along the longitudinal axis of said cannula.

15. The kit of claim 1, wherein said syringe includes a valve coupled thereto between said syringe and said injection needle, said valve being operable in an open position to permit passage of said biomaterial from the syringe under pressure, and in a closed position to maintain the pressure of the injected material into said needle.

16. The kit of claim 1, wherein said biomaterial is selected to have upon curing strong adhesive properties.

17. The kit of claim 1, wherein said biomaterial is selected to contain a protein polymer.

* * * * *